United States Patent [19]

Talbot

[11] Patent Number: 4,649,027
[45] Date of Patent: Mar. 10, 1987

[54] BREATH TESTER

[75] Inventor: Douglas C. Talbot, Vail, Colo.

[73] Assignee: CMI, Inc., Minturn, Colo.

[21] Appl. No.: 696,060

[22] Filed: Jan. 29, 1985

[51] Int. Cl.[4] .............................................. G01N 21/35
[52] U.S. Cl. ..................................... 422/84; 128/719;
250/343; 436/132; 436/900
[58] Field of Search .................... 73/23; 128/719, 717;
250/343; 356/437, 440; 422/84; 436/132, 900

[56] References Cited

U.S. PATENT DOCUMENTS

| | | | |
|---|---|---|---|
| 3,792,272 | 2/1974 | Harte et al. | 250/343 |
| 3,860,818 | 1/1975 | Stalder et al. | 250/343 |
| 3,861,809 | 1/1975 | Hall | 250/343 X |
| 4,008,614 | 2/1977 | Turner et al. | 374/209 X |
| 4,323,777 | 4/1982 | Baskins et al. | 250/343 X |

OTHER PUBLICATIONS

Drager: Alcotest 7010, publication 1981.

Primary Examiner—Barry S. Richman
Assistant Examiner—Michael S. Gzybowski
Attorney, Agent, or Firm—Charles F. Pigott, Jr.

[57] ABSTRACT

A battery-operated portable breath tester is disclosed. The breath tester includes a housing which defines a sleeve for receiving a wand. The wand defines an internal sample chamber, with a lamp at one end for providing infrared energy and a detector at an opposite end for receiving the infrared energy after it has passed through the sample to be tested. The wand defines opening extending from the internal sample chamber to the outside of the wand. The wand has an external shape providing a snug fit within the sleeve. As the wand is moved within the sleeve, gas is purged from the wand. The wand is connected to the housing by means of an electrical coil. The housing encloses a digital voltmeter including a digital display for providing a test readout. The digital voltmeter includes an oscillator which is coupled through a frequency divider and a transistor switch to the lamp. The lamp is switched on and off in accordance with the frequency output of the frequency divider to modulate the infrared energy emitted from the lamp at a selected frequency. A voltage regulator is connected to the lamp, and the lamp and voltage regulator are located in heat-exchange relationship with the sample chamber. This aids in raising the temperature of the sample chamber during testing in order to alleviate condensation.

25 Claims, 6 Drawing Figures

BREATH TESTER

BACKGROUND OF THE INVENTION

The present invention is a novel breath tester, for example of a type which can quantitatively evaluate the amount of alcohol in a person's breath.

Breath testers are used by police, in hospitals, schools, and in many other places where a determination of the quantity of alcohol in the blood is desired. Such breath testers measure the blood alcohol concentration through analysis of a breath sample. While the breath tester directly measures the alcohol in the breath and does not directly measure the alcohol in the blood, there is a mathematical correlation between the two.

Law enforcement agencies often use both evidentiary breath testers and preliminary breath testers. Evidentiary breath testers are relatively large and expensive and may be approved by the U.S. Department of Transportation for evidential use. In contrast, preliminary breath testers are typically smaller, less expensive, less accurate, and carried by police in their vehicles. They are used to enable the police officer to obtain a preliminary reading from the suspected drunk driver to enable the police officer to determine whether he should take the suspect to the police station.

I have discovered a need for a preliminary breath tester that is relatively small, lightweight, relatively inexpensive, but also significantly accurate. It is to be understood that my invention is applicable to evidentiary breath testers as well as to preliminary breath testers, although my invention enables a breath tester to be constructed which is efficient in size, weight and operation.

Certain prior art breath testers require a bellows pump or the like in order to purge the chamber of the sample contained therein. I have discovered a means for obviating the need for a bellows pump, thus simplifying the operation and making the structure more economical.

It is an object of the present invention to provide a breath tester that is efficient to manufacture and is simple in operation.

Another object of the present invention is to provide a breath tester that may be adapted for easy portability and may be carried by a police officer in a police car.

Other objects and advantages of the present invention will become apparent as the description proceeds.

SUMMARY OF THE INVENTION

In accordance with the present invention, a breath tester is provided which can be battery-operated and is portable. In the illustrative embodiment, the breath tester comprises a housing defining a sleeve adapted for receiving a wand. A wand is connected to the housing via an electrical coil. The wand defines an internal sample chamber. A lamp is positioned within the wand for providing infrared energy and a detector is located within the wand for receiving the infrared energy after it has passed through the sample to be tested.

The wand defines a plurality of openings extending from the internal sample chamber to the outside of the wand. The wand has an external shape which provides a snug fit within the sleeve. In this manner, as the wand is moved within the sleeve, gas is purged from the sample chamber via at least one of the wand openings.

In the illustrative embodiment, the sleeve defines a gas opening at a location adjacent the bottom of the sleeve. A valve is provided for blocking gas from entering the sleeve through the gas opening unless the wand is fully inserted therein. Once the wand is fully inserted therein, the gas opening of the sleeve is in communication with the wand opening and the breath may be tested with the wand fully positioned within the sleeve. On the other hand, the wand need not be positioned within the sleeve to receive the breath to be tested.

In the illustrative embodiment, the housing includes a battery and control circuitry. The control circuitry includes oscillating means which are coupled to the lamp for electronically modulating the infrared energy therefrom at a selected frequency.

In the illustrative embodiment, the oscillating means comprises a portion of a digital voltmeter. The digital voltmeter includes a digital display for providing a test readout. A frequency divider and a switching transistor are coupled to the lamp for switching the lamp on and off in accordance with the frequency of the output from the frequency divider.

In the illustrative embodiment, a voltage regulator is connected to the lamp. The voltage regulator and the lamp are located in heat-exchange relationship with the sample chamber to aid in raising the temperature of the sample chamber during testing to alleviate condensation.

A more detailed explanation of the invention is provided in the following description and claims, and is illustrated in the accompanying drawings.

DETAILED DESCRIPTION OF THE ILLUSTRATIVE EMBODIMENT

Figure 1:
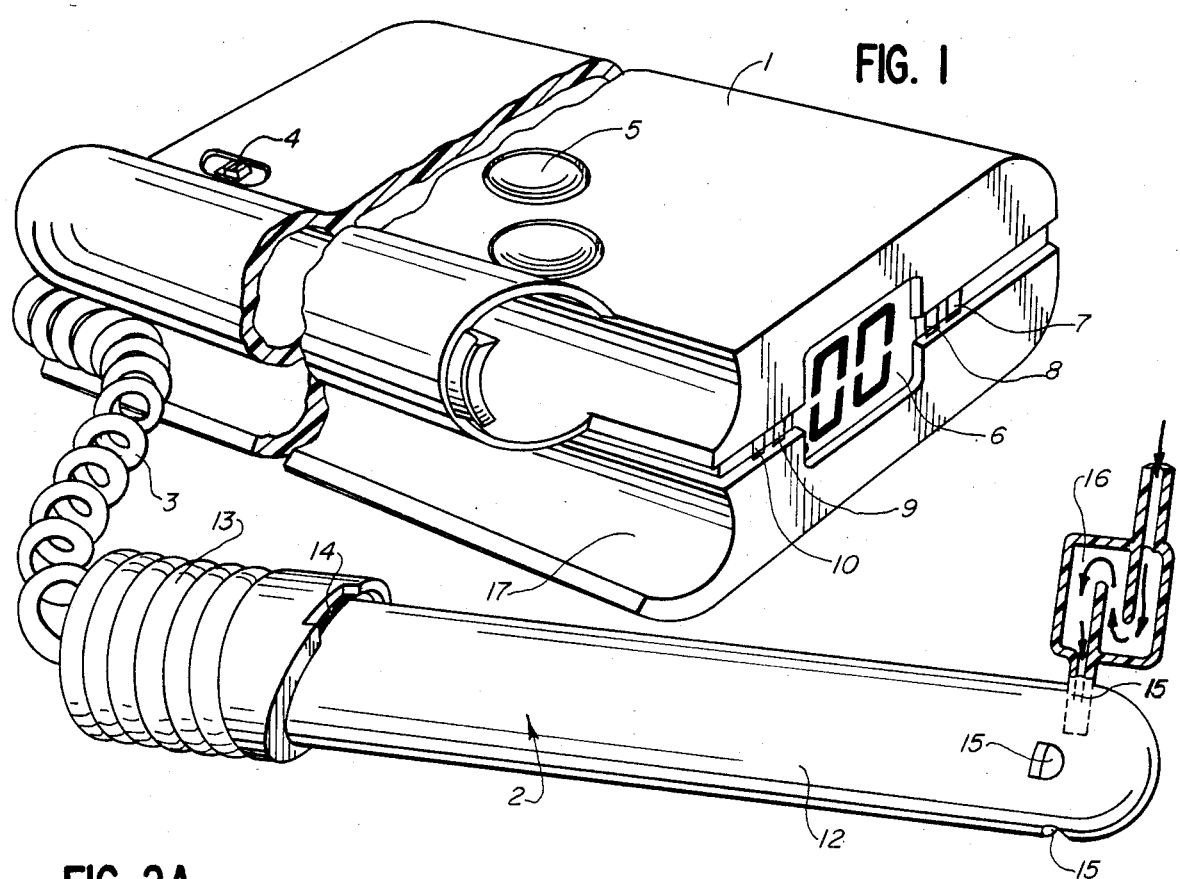
FIG. 1 is a perspective view, partially broken due to size limitations, of a breath tester constructed in accordance with the principles of the present invention.

Referring to FIG. 1, the breath tester comprises a housing 1 having a wand 2 connected thereto via an electrical coil 3. The housing includes an on/off switch 4, an advance button 5, a digital readout 6, a first "power" light-emitting diode (LED) 7, a second "low battery condition" LED 8, a third "test" LED 9, and a fourth "hold" LED 10. The operation of LEDs 7, 8, 9 and 10 will be discussed in more detail below.

The housing defines a sleeve 11, which has a generally circular cross-sectional configuration and an internal diameter that is substantially equal to the external diameter of the main portion 12 of wand 2. Thus main portion 12 of wand 2, which has a circular cross-sectional configuration, fits into sleeve 11 with a snug fit. Wand 2 has a handle 13 and defines an opening 14 adjacent its forward end and also a number of openings 15 adjacent its distal end. Openings 15 are adapted for receiving a spit trap 15.

The housing also defines a curved recessed area 17 for receiving the coil 3 when the unit is assembled with the wand 2 inserted into sleeve 11.

Figure 3:
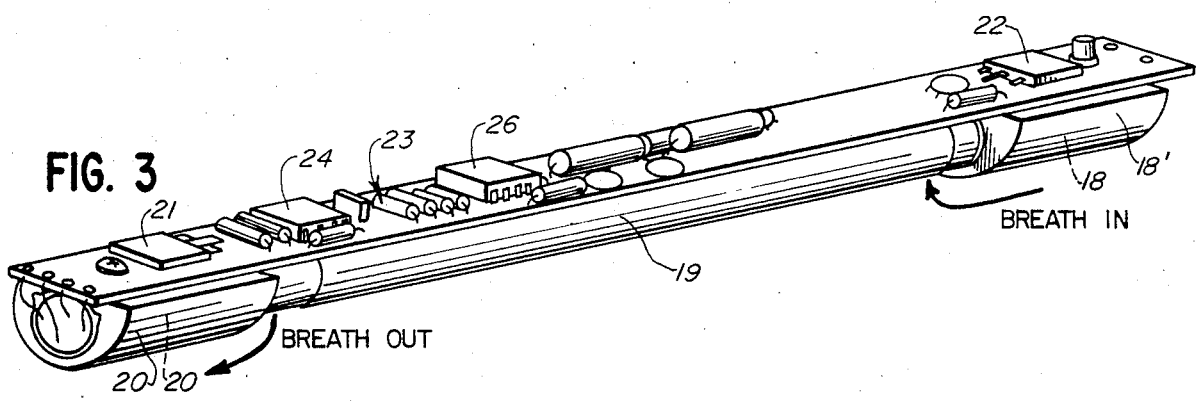
FIG. 3 is a perspective view of the interior of the wand.

The interior of wand 2 is illustrated in FIG. 3. Referring to FIG. 3, there is a lamp 18 located within a lamp housing 18' at one end of a sample chamber 19, and a detector 20 located within a detector housing 20' at the other end of the sample chamber 19. Lamp 18 is a lamp for providing infrared energy, preferably a quartz halogen lamp. The lamp is modulated at a selected frequency, such as 30 hertz, and it is significant that it have a quick response to enable such modulation, and that it have sufficient energy emitted at a selected wavelength. In the illustrative embodiment, the selected wavelength is 3.4 microns which is a useful wavelength for detecting alcohol.

In one embodiment, an incandescent lamp may be used. Although no limitation is intended, the incandescent lamp could comprise a Gilway 1021 bulb which contains a built-in lens for focusing the beam. If the lamp bulb used does not have a built-in lens, it is appropriate to use a lens to focus the beam through the cell thereby improving the signal to noise ratio.

Detector 20, at the other end of cell 19, is preferably a lead selenide detector with a built-in temperature compensation thermistor and also a built-in narrow band optical filter centered at the selected wavelength, for example, 3.4 microns.

Lamp 18 is placed in effective heat exchange contact with sample cell 19 at one end thereof. A voltage regulator 21, to be described in more detail below, is also placed in heat exchange relationship with the sample chamber 19 at the other end thereof, adjacent detector 20, in order to alleviate condensation by raising the temperature of the chamber above breath temperature. By using the heat of lamp 18 and heat derived from voltage regulator 21 to aid in heating up the cell, it is unnecessary to utilize any other heating means. In this manner, substantial current is saved because the energy that would normally be wasted is being used to heat the sample cell. The lamp output is controlled by a switching transistor 22 and the detector is coupled to processing circuit 23 including a FET input op amp 24 and a low noise gain stage 26. The circuitry will be discussed in more detail below.

Figure 2A:
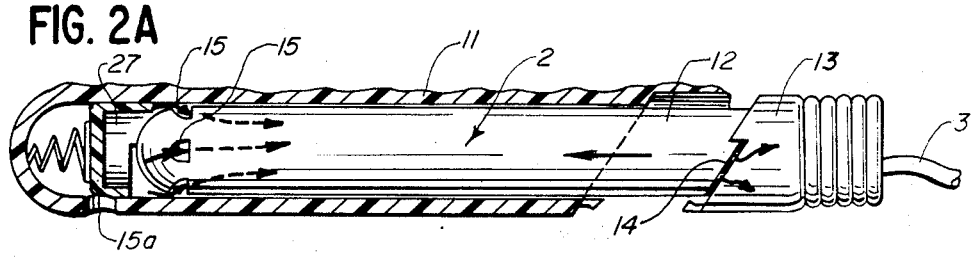
FIG. 2A is a view of the wand of FIG. 1 being inserted into the sleeve.
Figure 2B:
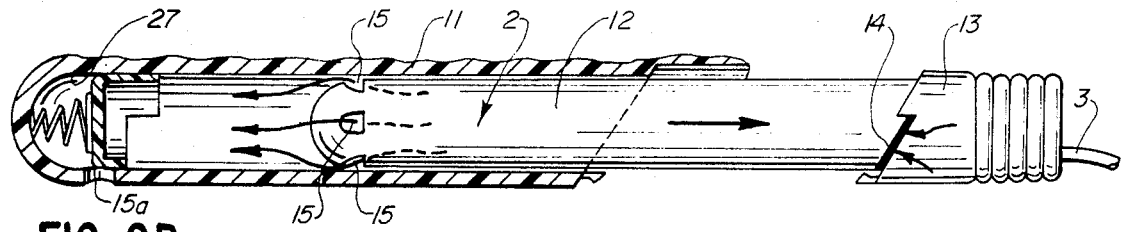
FIG. 2B is a view of the wand being withdrawn from the sleeve.

Referring to FIGS. 2A and 2B, sleeve 11 defines an opening 15a adjacent its bottom. A spring-biased valve member 27 normally overlies opening 15a to prevent air from entering the sleeve. However, if wand 2 is inserted all of the way into sleeve 11, valve member 27 will be urged forwardly by the wand to clear opening 15a. Opening 15a may then be in communication with one of the openings 15 of wand 2, which openings 15 are in communication with the sample cell 19. Thus when wand 2 is completely inserted into sleeve 11, the spit trap 16 can be inserted into opening 15a and it will thus extend into one of the openings 15 of wand 2 to enable a breath sample to be taken, if desired, while the wand 2 is inside sleeve 11.

Normally, the breath sample will be taken while the wand is outside of the sleeve, as illustrated in FIG. 1. Once the breath sample has been taken, the system will be reset only when the wand is completely inserted into sleeve 11. To this end, an optical device is provided at the bottom of sleeve 11. The optical device will be activated when valve member 27 moves into its path, thus operating to reset the circuit.

Prior to the present invention, a bellows pump or the like was typically used to clear the chamber of the previous sample. In accordance with the present invention, when the wand is inserted into the sleeve, as illustrated in FIG. 2A, the air that is in the sleeve is forced into the chamber 19 via openings 15 and this air pushes the remaining tested gas out of the sample chamber via slot 14. When the wand 2 is withdrawn from the sleeve 11, as illustrated in FIG. 2B, a low pressure condition is created within the sleeve to draw the air out of the sample chamber via openings 15.

Figure 4:
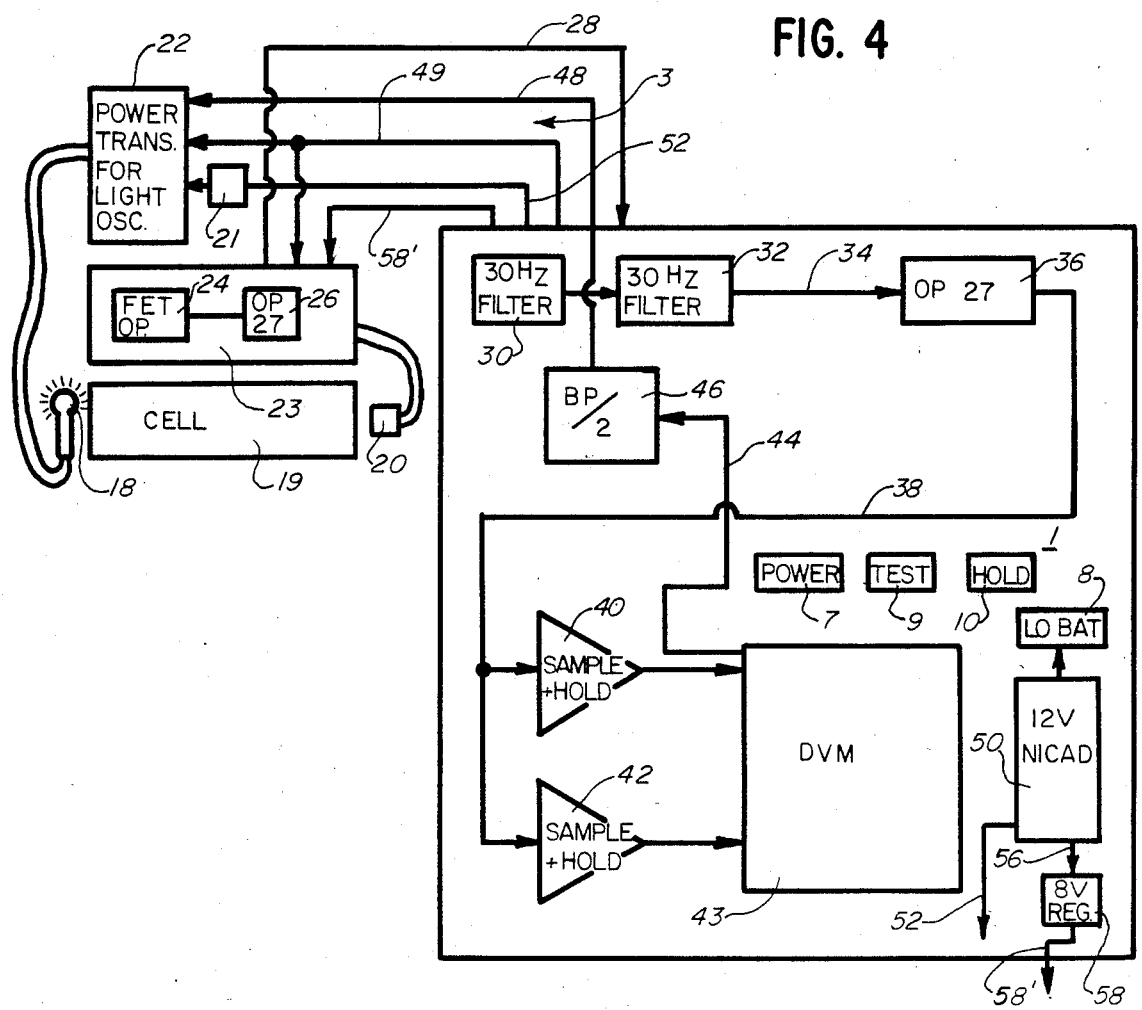
FIG. 4 is a block diagram of the electrical circuitry for the breath tester of FIG. 1.

A block diagram of the system circuitry is presented in FIG. 4. Referring to FIG. 4, the left-hand side shows the wand circuitry, including lamp 18, cell 19, detector 20, voltage regulator 21, transistor 22, processing circuit 23, FET input op amp 24 and low noise gain stage 26. The wand components are connected to the housing 1 via electrical coil 3, with the processing circuitry 23 being coupled to circuitry within the housing 1 by means of line 28.

The circuit within housing 10 includes a 30 hertz filter 30, the output of which is coupled to a second 30 hertz filter 32. Both 30 hertz filters 30, 32 are stacked in order to increase the Q. The output of the filters is connected via line 34 to an op amp 36 in order to amplify the signal to approximately the supply voltage.

The amplified signal is fed via line 38 to two sample and hold circuits 40 and 42. The outputs of the sample and hold circuits 40, 42 are connected to a digital voltmeter 43. The digital voltmeter 43 comprises an integrated circuit chip having a high and a low input. When in any mode other than the test mode, both sample and hold circuits 40 and 42 are provided with the same input and have the same output to digital volt meter 43, whereby the readout (on display 6) will be zero. When in the test mode, sample and hold circuit 40 is frozen, allowing sample and hold circuit 42 to provide the voltage to digital voltmeter 43 for providing an appropriate readout on display 6.

Digital voltmeter 43 includes an analog to digital converter and also has the drive circuitry to drive the digital display 6. The digital volt meter 43 includes an oscillator and there is a back plane output line 44 from chip 43 which is divided to provide 30 hertz from divider 46. The 30 hertz voltage signal is fed via line 48 to power transistor 22. The housing includes a 12 volt nickel cadmium rechargeable battery 50, with a 9.2 volt output line 52 which is connected to a 5 volt voltage regulator 21. The output of voltage regulator 21 is connected to the power transistor 22. There is also a 12 volt output line 56 from battery 50 which is connected to an 8 volt voltage regulator 58. An 8 volt regulated line 58' provides an 8 volt regulated voltage to preamplifier 23 via line 58'.

In the test mode, sample and hold circuit 40 is frozen and sample and hold circuit 42 provides a voltage to the digital voltmeter 43. When the unit goes into the hold mode, hold LED 10 is energized and sample and hold circuit 42 is frozen so that there will be a frozen display of the test value on display 6.

Figure 5:
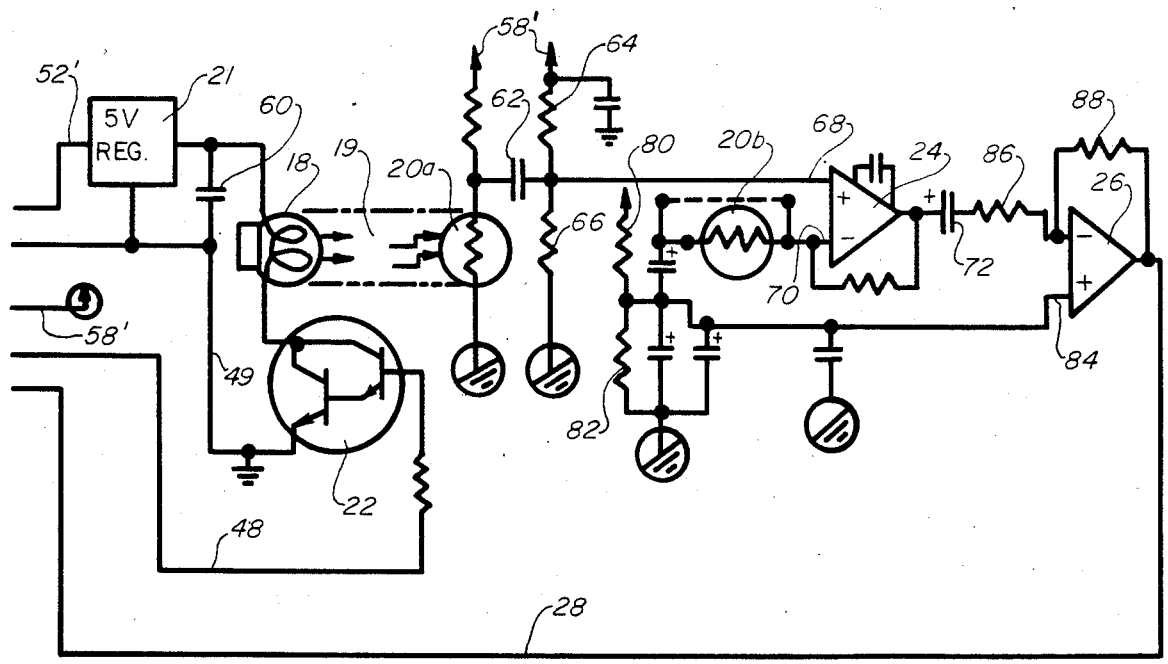
FIG. 5 is a schematic circuit diagram of the wand circuitry.

FIG. 5 illustrates the wand circuitry in detail. Referring to FIG. 5, lamp 18 is driven by a Darlington transistor pair 22 having a 30 hertz voltage at the base of the transistor pair 22. The output of the 5 volt voltage regulator 21 is coupled to one side of the filament of lamp 18, with the other side of the filament of lamp 18 being connected to the switching transistor 22. Line 48 is from the divided signal from digital voltmeter 43 and carries the 30 hertz signal to turn the switching transistor 22 on and off, thereby pulling lamp 18 to ground at 30 cycles per second. At the output of voltage regulator 21, there is a bypass capacitor 60 which is used to obviate noise.

Detector 20 comprises a lead selenide detector 20a and a thermistor 20b which is isolated by capacitor 62. A voltage divider comprising resistors 64 and 66 is used to hold input 68 of op amp 24 at a certain input level, for example, one-half of the supply voltage. The negative input 70 to op amp 24 is also referenced to one-half the supply voltage. Therefore, there is normally no output until detector 20a provides an AC voltage output which corresponds to the infrared energy from energy source 18 passing through the gas within cell 19. The output of op amp 24 is AC coupled via capacitor 72 to another op amp 26 for additional gain. The output signal from op amp 26 is fed line 28 to a 30 hertz filter 30 which is in housing 1.

A voltage divider comprising resistor 80 and resistor 82 is used to provide an appropriate reference voltage for the positive input 84 of op amp 26. Resistors 86 and 88 provide the appropriate gain to the op amp 26.

In order for the 5 volt voltage regulator 21 to operate properly, there must be an input of at least 8 volts. As a result of the voltage drop of at least three volts, some heat is given off by voltage regulator 21. As stated above, voltage regulator 21 is placed in heat exchange relationship with the chamber 19 to alleviate condensation by raising the temperature of the chamber above breath temperature. Further, bulb 18 also gives off some heat and the body of the bulb 18 is in heat exchange contact with the cell 19 to aid in heating the cell.

In the operation of the device, the unit is turned on by a switch 4 (FIG. 4). The power LED 7, which is red, is energized and it will remain energized for several minutes while the unit warms up. When the unit has reached the operating temperature, no LEDs will be energized; only the display 6 will be showing 0.00. The wand 2 can then be withdrawn from sleeve 11 and the subject requested to provide his breath for the test. The advance button 5 is then pressed and the subject will provide breath to the chamber 19 via the spit trap 16. During the test, the test LED 9, which is green, is energized, and the digital display 6 will be increasing to show the alcohol content. At any time, the advance button 5 may be pressed again, to freeze the readout. Once the readout is frozen, the hold LED 10, which is amber, will be energized.

Red LED 8 is used to indicate when there is a low battery condition.

The system also contains a circuit that has a slope detector, in order to determine when the deep lung air has been reached. It can be seen that the placing of the wand into and out of the sleeve is irrelevant to the testing and is primarily for the purpose of convenience and for the purpose of purging the previously sampled breath. It also serves to enter an ambient air sample into the chamber.

In a specific example, a breath tester according to the illustrative embodiment weighed slightly over two pounds and was approximately 10 inches long by approximately 4 inches wide and less than 2 inches deep. Sample chamber 19 was 6 inches long and did not use any reflection. Instead, the modulated lamp beam was transmitted straight through the elongated chamber 19.

Although an illustrative embodiment of the invention has been shown and described, it is to be understood that various modifications and substitutions may be made by those skilled in the art without departing from the novel spirit and scope of the present invention.

What is claimed is:

1. A breath tester which comprises:
   a housing defining a sleeve adapted for receiving a wand;
   a wand defining an internal sample chamber for receiving a sample, a lamp within the wand for providing infrared energy, and a detector in the wand for receiving the infrared energy after it has passed through the sample to be tested;
   means for purging gas from said internal sample chamber, said purging means comprising means defining a pair of spaced apart openings located in a main portion of the wand and extending therethrough whereby said internal sample chamber communicates with the environment outside of the wand, said wand having an external shape to provide a snug fit within the sleeve whereby movement of said wand within said sleeve creates necessary pressures and vacuums required to purge gas from said sample chamber without a mechanical pump.

2. A breath tester as described in claim 1, wherein said sleeve has means defining a gas opening at a location adjacent to a bottom of said sleeve and a valve located adjacent said gas opening for blocking gas from entering said sleeve through said gas opening unless said wand is fully inserted into said sleeve whereby, when said wand is fully inserted into said sleeve, said gas opening of said sleeve is aligned in communication with a wand opening.

3. A breath tester as described in claim 1, wherein said sleeve includes means for sensing when the wand has been fully inserted therein.

4. A breath tester as described in claim 1, including an electrical wire connecting said wand to said housing, said housing including a battery and oscillating means therein; and means coupling said oscillating means to said lamp for electronically modulating the infrared energy therefrom at a selected frequency, said coupling means including means for switching said lamp on and off in accordance with the selected frequency.

5. A breath tester as described in claim 1, wherein said openings comprise a first opening adjacent a distal end of the wand and a second opening adjacent an opposite end of the wand, whereby withdrawal of the wand from the sleeve creates a low pressure condition in the sleeve to draw gas from the internal sample chamber out of the wand via said first opening, and insertion of the wand into the sleeve operates to force gas from the internal sample chamber out of the wand via said second opening.

6. A breath tester as described in claim 5, wherein said sleeve has means defining a gas opening at a location adjacent to a bottom of said sleeve and a valve located adjacent said gas opening for blocking gas from entering said sleeve through said gas opening unless said wand is fully inserted into said sleeve whereby, when said wand is fully inserted into said sleeve, said gas opening of said sleeve is aligned in communication with a wand opening.

7. A breath tester as described in claim 1, including an electrical wire connecting said wand to said housing, said housing including a battery and control circuitry therein, said control circuitry including oscillating means; and means coupling said oscillating means to said lamp for electronically modulating the infrared energy therefrom at a selected frequency.

8. A breath tester as described in claim 7, wherein said coupling means includes a frequency divider and means for switching said lamp on and off in accordance with the frequency of the output from the frequency divider.

9. A breath tester as described in claim 1, including means positioning said lamp in heat exchange relationship with said sample chamber to aid in raising the temperature of said sample chamber during testing to inhibit condensation of the sample within the sample chamber.

10. A breath tester as described in claim 9, including a voltage regulator connected to said lamp, means positioning said voltage regulator in heat exchange relationship with said sample chamber to aid in raising the temperature of said sample chamber during testing to inhibit condensation of the sample within the sample chamber.

11. A breath tester which comprises:
a housing defining a sleeve adapted for receiving a wand;
a wand defining an internal sample chamber, said wand being positionable in a sleeve;
a lamp within said wand for providing infrared energy;
a detector for receiving the infrared energy after it has passed through a sample to be tested;
means for purging gas from said internal sample chamber without requiring a mechanical pump, said purging means comprising said wand having means defining a pair of spaced openings extending from said internal sample chamber to the outside of the wand, said wand having an external shape to provide a snug fit within said sleeve, whereby movement of said wand within said sleeve effectuates purge of the gas within said sample chamber without requiring a mechanical pump;
said openings comprising a first opening adjacent a distal end of the wand and a second opening adjacent an opposite end of the wand, whereby withdrawal of the wand from the sleeve creates a low pressure condition in the sleeve to withdraw gas from the internal sample chamber out of the wand via said first opening, and insertion of the wand into the sleeve operates to force gas from the internal sample chamber out of the wand via said second opening;
an electrical wire connecting said wand to said housing;
said housing including a battery and control circuitry;
said control circuitry including oscillating means;
means coupling said oscillating means to said lamp for electronically modulating the infrared energy therefrom at a selected frequency;
said coupling means including a frequency divider and means for switching said lamp on and off in accordance with the frequency of the output from the frequency divider.

12. A breath tester which comprises:
a wand defining an internal sample chamber;
a sleeve configured to enable positioning of said wand therein;
a lamp within said wand for providing infrared energy;
a detector for receiving the infrared energy after it has passed through a sample to be tested;

means for purging gas from said internal sample chamber without requiring a mechanical pump, said purging means comprising said wand having means defining a pair of spaced openings extending from said internal sample chamber to the outside of the wand, said wand having an external shape to provide a snug fit within the sleeve, whereby movement of said wand within the sleeve effectuates purge of the gas within said sample chamber without requiring a mechanical pump;
a digital voltmeter including a digital display for providing a test readout;
said digital voltmeter including an oscillator having an output;
a frequency divider coupled to the output of said oscillator;
switching means; and
means coupling said frequency divider and switching means to said lamp for switching said lamp on and off in accordance with the frequency output of the frequency divider.

13. A breath tester as described in claim 12, including a battery for powering said digital voltmeter and said lamp; and
a sample and hold circuit for freezing the test readout displayed by said digital display.

14. A breath tester as described in claim 12, said switching means comprising a Darlington transistor pair connected in series with the lamp and the output of the frequency divider.

15. A breath tester as described in claim 12, including a voltage regulator connected to said lamp, means positioning said voltage regulator in heat exchange relationship with said sample chamber to aid in raising the temperature of said sample chamber during testing to inhibit condensation of the sample within the sample chamber.

16. A breath tester as described in claim 15, including means positioning said lamp in heat exchange relationship with said sample chamber to aid in raising the temperature of said sample chamber during testing to inhibit condensation of the sample within the sample chamber.

17. A breath tester as described in claim 12, including first signal amplifying means connected to the output of said detector; filter means for passing only the amplified signal having the lamp-switching frequency to second signal amplifying means;
said second signal amplifying means being operative to amplify the signal to approximately the supply voltage to segregate the signal from noise.

18. A breath tester as described in claim 17, including a sample and hold circuit connected to the output of said second signal amplifying means and to the input of said digital volt meter for freezing a test value displayed by said digital display.

19. A breath tester which comprises:
a wand defining an internal sample chamber; a sleeve configured to enable positioning of said wand therein;
a lamp within said wand for providing infrared energy;
a detector for receiving the infrared energy after it has passed through a sample to be tested;
means for purging gas from said internal sample chamber without requiring a mechanical pump, said purging means comprising said wand having means defining a pair of spaced openings extending from said internal sample chamber to the outside of the wand, said wand having an external shape to provide a snug fit within the sleeve, whereby movement of said wand within the sleeve effectuates purge of the gas within said sample chamber without requiring a mechanical pump;

a digital voltmeter including a digital display for providing a test readout;

said digital voltmeter including an oscillator;

a frequency divider coupled to the output of said oscillator;

switching means;

means coupling said frequency divider and switching means to said lamp for switching said lamp on and off in accordance with the frequency output of the frequency divider;

a battery for powering said digital voltmeter and said lamp;

a sample and hold circuit for freezing the test value displayed by said digital display;

a voltage regulator connected to said lamp;

means positioning said lamp and voltage regulator in heat exchange relationship with said sample chamber to aid in raising the temperature of said sample chamber during testing to suppress condensation;

first signal amplifying means connected to the output of said detector;

filter means for passing the amplified signal having the lamp-switching frequency to said second signal amplifying means;

said second signal amplifying means being operative to amplify the signal to approximately the supply voltage to segregate the signal from noise.

20. A portable breath tester which comprises:

a wand defining an internal sample chamber; a sleeve configured to enable positioning of said wand therein;

a lamp within said wand for providing infrared energy;

a detector for receiving the infrared energy after it has passed through a sample to be tested;

means for purging gas from said internal sample chamber without requiring a mechanical pump, said purging means comprising said wand having means defining a pair of spaced openings extending from said internal sample chamber to the outside of the wand, said wand having an external shape to provide a snug fit within the sleeve, whereby movement of said wand within the sleeve effectuates purge of the gas within said sample chamber without requiring a mechanical pump;

electronic oscillating means;

switching means;

means coupling said electronic oscillating means and switching means to said lamp for switching said lamp on and off in accordance with the frequency output of said oscillating means.

21. A portable breath tester as described in claim 20, including means positioning said lamp in heat-exchange relationship with said sample chamber to aid in raising the temperature of said sample chamber during testing to inhibit condensation of the sample within the sample chamber.

22. A portable breath tester as described in claim 20, including a voltage regulator connected to said lamp, means positioning said voltage regulator in heat-exchange relationship with said sample chamber to aid in raising the temperature of said sample chamber during testing to inhibit condensation of the sample within the sample chamber.

23. A portable breath tester as described in claim 20, including first signal amplifying means connected to the output of said detector;

filter means for passing only the amplified signal having the lamp-switching frequency to second signal amplifying means;

said second signal amplifying means being operative to amplify the signal to approximately the supply voltage to segregate the signal from noise.

24. A portable breath tester as described in claim 23, including a sample and hold circuit connected to the output of said second signal amplifying means for freezing a test value that is displayed.

25. A battery-operated portable breath tester which comprises:

a wand defining an internal sample chamber; a sleeve configured to enable positioning of said wand therein;

a lamp with said wand for providing infrared energy;

a detector for receiving the infrared energy after it has passed through a sample to be tested;

means for purging gas from said internal sample chamber without requiring a mechanical pump, said purging means comprising said wand having means defining a pair of spaced openings extending from said internal sample chamber to the outside of the wand, said wand having an external shape to provide a snug fit within the sleeve, whereby movement of said wand within the sleeve effectuates purge of the gas within said sample chamber without requiring a mechanical pump;

a battery for powering the breath tester;

oscillating means;

switching means;

means coupling said oscillating means and switching means to said lamp for switching said lamp on the off in accordance with the frequency output of the oscillating means;

a digital voltmeter including a digital display for providing a test readout;

a voltage regulator connected to said lamp;

means positioning said lamp and said voltage in heat-exchange relationship with said sample chamber to aid in raising the temperature of said sample chamber during testing to alleviate condensation;

first signal amplifying means connected to the output of said detector;

filter means for passing only the amplified signal having the lamp-switching frequency to second signal amplifying means;

said second signal amplifying means being operative to amplify the signal to approximately the supply voltage to segregate the signal from noise; and a sample and hold circuit connected to the output of said second signal amplifying means and to the input of said digital voltmeter for freezing a test value displayed by said digital display.

* * * * *